United States Patent [19]

Schirlin et al.

[11] Patent Number: 5,532,397

[45] Date of Patent: Jul. 2, 1996

[54] SUBSTITUTED SILYL ALKYLENE AMINES

[75] Inventors: Daniel G. Schirlin, Lampertheim; Jean-Noël Collard, Balbronn; Charles Danzin, Strasbourg, all of France

[73] Assignee: Merrell Pharmaceuticals Inc., Cincinnati, Ohio

[21] Appl. No.: 310,188

[22] Filed: Sep. 21, 1994

Related U.S. Application Data

[60] Division of Ser. No. 875,938, Apr. 30, 1992, which is a continuation-in-part of Ser. No. 690,431, Apr. 24, 1991, abandoned, which is a continuation of Ser. No. 500,446, Mar. 28, 1990, abandoned, which is a continuation-in-part of Ser. No. 463,850, Jan. 12, 1990, abandoned, which is a continuation of Ser. No. 178,113, Apr. 19, 1988, abandoned, which is a continuation-in-part of Ser. No. 47,847, May 8, 1987, abandoned.

[51] Int. Cl.$^6$ ........................................... C07F 7/10
[52] U.S. Cl. .................... 556/413; 556/415; 556/422; 556/423
[58] Field of Search ................. 556/413, 415, 556/422, 423; 524/63

[56] References Cited

U.S. PATENT DOCUMENTS

| | | | |
|---|---|---|---|
| 2,557,802 | 6/1951 | Sommer | 556/413 |
| 2,754,311 | 7/1956 | Elliott | 556/413 |
| 3,066,060 | 11/1962 | Gross | 556/413 X |
| 5,089,518 | 2/1992 | Trybulski et al. | 514/63 X |
| 5,185,328 | 2/1993 | Fukikawa et al. | 514/63 |

Primary Examiner—Paul F. Shaver
Attorney, Agent, or Firm—Stephen L. Nesbitt

[57] ABSTRACT

This invention relates to substituted silyl alkylene amines, to the intermediates and processes useful for their preparation, to their pharmacological use as MAO-B inhibitors and to their end-use application in the treatment of Parkinson's Disease and senile dementia of Alzheimer's type.

17 Claims, No Drawings

SUBSTITUTED SILYL ALKYLENE AMINES

This is a division, of application Ser. No. 07/875,938, filed Apr. 30, 1992, now allowed, which is a continuation-in-part of application Ser. No. 07/690,431, filed Apr. 24, 1991, now abandoned, which is a continuation of application Ser. No. 07/500,446, filed Mar. 28, 1990, now abandoned, which is a continuation-in-part of application Ser. No. 07/463,850, filed Jan. 12, 1990, now abandoned, which is a continuation of application Ser. No. 07/178,113, filed Apr. 19, 1988, now abandoned, which is a continuation-in-part of application Ser. No. 07/047,847, filed May 8, 1987, now abandoned, which are herein incorporated by reference.

This invention relates to substituted silyl alkylene amines, to the intermediates and processes useful for their preparation, to their pharmacological use as MAO-B inhibitors and to their end-use application in the treatment of Parkinson's Disease and of senile dementia of Alzheimer's type (DAT or SDAT).

More specifically this invention relates to substituted silyl alkylene amines of the formula

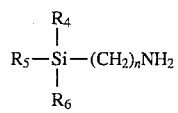
                                                        I and the pharmaceutically acceptable salts thereof, wherein n is an integer 1 or 2, $R_4$ is $C_{1-10}$ alkyl, $R_5$ is $C_{1-10}$ alkyl or $-(CH_2)_m-X,Y$-substituted aryl, $R_6$ is cyclohexylmethyl or $-(CH_2)_m-X,Y$-substituted aryl, with each of X and Y being H, OH, halogens, $C_{1-6}$ alkyl, $C_{1-6}$ alkoxy, $CF_3$, CN or $NO_2$, and m is an integer 1 to 4, with the proviso that the

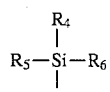

moiety is other than benzyldimethylsilyl or benzyldiethylsilyl.

As used herein the term $C_{1-10}$ alkyl includes the straight, branched-chain and cyclized manifestations thereof, particularly such moieties as methyl, ethyl, n-butyl, t-butyl, cyclopropyl, n-propyl, pentyl, n-hexyl, n-nonyl, decyl, cyclopentyl, cyclohexylmethyl and cyclohexyl The term "aryl", within the definitions of the $R_5$ and $R_6$ groups, includes both carbocyclic and heterocyclic moieties of which phenyl, pyridyl, indolyl, indazolyl, furyl and thienyl are of primary interest. Preferably m is 1, except when aryl is phenyl, then it is 1 or 2. Of course, these moieties include all of the position isomers thereof such as, for example, 2-, 3-, or 4-pyridyl, 2- or 3-furyl, 2- or 3-thienyl, 1-, 2- or 3-indolyl, and the 1- and 3-indazolyl, as well as the dihydro and tetrahydro analogs of the furyl and thienyl moieties.

Halogens includes all four members of the group with fluoro and chloro being preferred and with fluoro being most preferred. When X and/or Y are other than H, the substituents may be located at any of the normally acceptable positions. In those instances wherein aryl is phenyl, the scope preferably includes mono and disubstituted moieties, particularly wherein one or both substituents are fluoro. Specially preferred $-(CH_2)_m$ X,Y-substituted aryl moieties are the 2-fluoro, 3-fluoro, 4-fluoro, 2,4-difluoro, 2,6-difluoro or the 3,4-difluorobenzyl or phenethyl moieties.

The pharmaceutically acceptable salts of the compounds of formula I include salts formed with non-toxic organic or inorganic acids such as, for example, from the following acids: hydrochloric, hydrobromic, sulfonic, sulfuric, phosphoric, nitric, maleic, fumaric, benzoic, ascorbic, pamoic, succinic, methanesulfonic acid, acetic, propionic, tartaric, citric, lactic, malic, mandelic, cinnamic, palmitic, iraconic and benzenesulfonic.

The preparation of the compounds of formula I are effected by a variety of procedures depending primarily upon the specific definitions of the n and $R_4$, $R_5$ and $R_6$ moieties. In any event, the chemical reactions and procedures are analogously known in the art and the selection of a particular route to obtain any particular specific type of compound is governed by principles well known and appreciated by those of ordinary skill in the art.

The following routes of synthesis will serve to teach those of ordinary skill in the art how the compounds of formula I may be prepared.

For the most part the procedures utilize silyl derivatives obtained from tetrachlorosilane ($SiCl_4$) or trichlorochlormethyl silane ($Cl_3SiCH_2Cl$) or a tailored modification thereof as starting materials. In essence these silyl derivatives are of the formulae

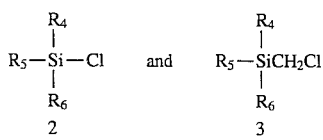
      2                    3 with $R_4$, $R_5$ and $R_6$ being as defined for formula I or they are in a reaction-protected form of the $R_4$, $R_5$, and $R_6$ substituents. (N. B. For convenience, the

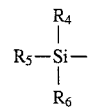

moiety may hereinafter be referred to as the $R_4R_5R_6Si$ moiety.) The preparation of the $R_4$, $R_5$ and $R_6$ substituted silanes of formulae 2 and 3 is readily effected by successive alkylations of tetrachloro-silane and trichlorochloromethyl silane using organo-magnesium halide derivatives of the appropriate $R_4$, $R_5$ and/or $R_6$ substituents. For example, $SiCl_4$ is reacted with $R_4Mg$ halides to produce $R_4SiCl_3$ compounds which are reacted with $R_5Mg$ halides to produce $R_4R_5SiCl_2$ compounds which are reacted with $R_6Mg$ halides to produce $R_4R_5R_6SiCl$ compounds. Analogously, $R_4Si(Cl_2)CH_2Cl$, $R_4R_5Si(Cl)CH_2Cl$ and $R_4R_5R_6SiCH_2Cl$ compounds are prepared by these successive alkylation procedures utilizing $Cl_3SiCH_2Cl$ as a starting reactant.

In the instance wherein it is desired to prepare compounds of formula I wherein n is one, the appropriate $R_4R_5R_6$ silyl methyl chloride 3 is subjected to a displacement reaction by treatment with potassium phthalimide or sodium azide to obtain the corresponding phthalimide or azide. Conversion of the phthalimide to the desired amine is by reaction with hydrazine hydrate and conversion of the azide is through chemical reduction to its amine, and subsequent purification of the so-prepared amines may be accomplished via its N-Boc derivative which is converted to the amine by hydrolysis. These reactions are depicted in Reaction Schemes A-1 and A-2.

Reaction Scheme A-1

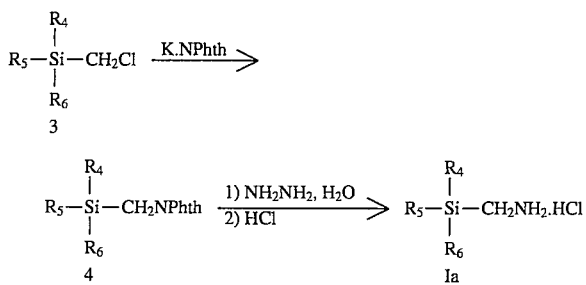

wherein $R_4$, $R_5$, $R_6$ are as defined in formula I and NPhth is a phthalimide moiety.

In effecting the foregoing reaction, the formation of the phthalimide is readily accomplished by standard reaction conditions for the displacement reaction, preferably by heating the reactants in an inert solvent, e.g., dry dimethylformamide at 70° C. The conversion of the phthalimide to its corresponding amine is effected by reaction with hydrazine hydrate in a suitable solvent, preferably ethanol, followed by treatment with aqueous acid, preferably HCl, under reflux conditions.

Reaction Scheme A-2

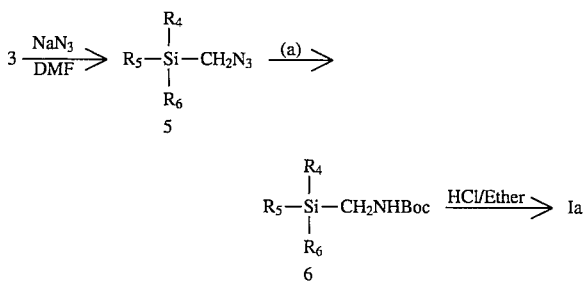

wherein (a) represents the sequential steps using (1) $P\varnothing_3$, THF, room temperature, (2) $H_2O$ and (3) $(BOC)_2O$, THF; and $R_4$, $R_5$, and $R_6$ are as defined in formula I, and $P\varnothing_3$ is triphenylphosphine.

In effecting the foregoing reaction (A-2) the formation of the azide is readily accomplished by standard reaction conditions for the displacement reaction, preferably by heating the reactants in an inert solvent (e.g., dry dimethylformamide) at 40° C. The conversion of the azide (5) to the corresponding amine (Ia) is effected through its N-Boc derivative (6) by the sequential treatment with (1) triphenylphosphine ($P\varnothing_3$) about room temperature in tetrahydrofuran (THF) (2) treatment with water followed by (3) purification of the desired product by the formation of its N-t-butoxycarbonyl derivative by reaction with $(BOC)_2O$ in THF at room temperature The N-Boc derivative is converted to its amine HCl salt (Ia) by reaction with gaseous HCl in diethylether (i.e., 3N HCl in diethylether) at room temperature.

In those instances wherein it is desired to prepare compounds of formula I wherein n is 2, esters (7) derived from the appropriate silylchloride (2) are reduced to their corresponding alcohols (8), preferably with lithium aluminum hydride and the alcohols are converted to their corresponding phthalimides (9) using Mitsunobu reaction conditions (i.e., treatment of the alcohol with diethylazodicarboxylate, triphenyl phosphine and phthalimide). The resulting phthalimides (9) are hydrolized to the corresponding amine hydrochloride by sequential reaction with hydrazine hydrate and aqueous HCl as described in Reaction Scheme A. The esters (7) are prepared by alkylation of (2) with a metallo derivative (preferably zinc or sodium) of ethyl acetate according to standard and well known conditions. This series of reactions is depicted in the following reaction scheme.

Reaction Scheme B

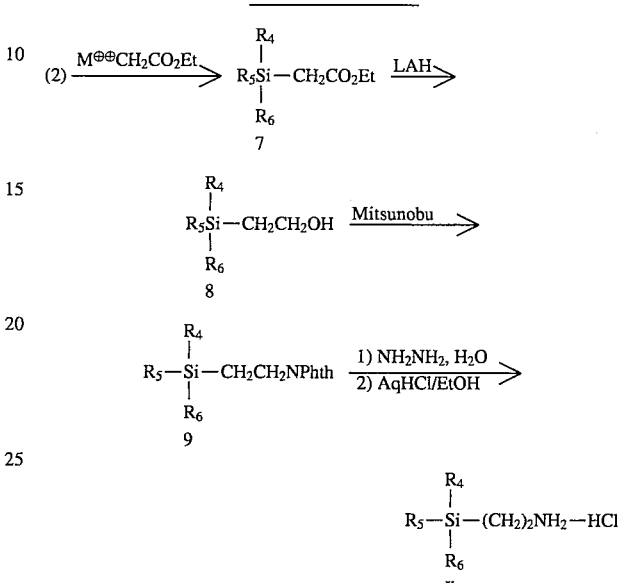

wherein $M^{\oplus}$ is a metallo cation of zinc or sodium, and $R_4$, $R_5$, $R_6$ and NPhth are as previously defined.

Alternatively, compounds (3) may be reacted with magnesium in diethylether to form the appropriate Grignard reagent which when treated with formaldehyde, (preferably using paraformaidehyde), will yield compounds of formula 8.

As described herein, the final steps utilized in the preparation of the compounds of formula I entails the removal of N-protecting groups to form the free amine and/or pharmaceutically acceptable salts thereof. Quite obviously the preferred N-protecting groups are the phthalimide and the t-butoxycarbonyl (Boc) groups. However, other equivalently functioning protecting groups may also be utilized and thus are included herein under the doctrine of equivalents.

The following examples serve to illustrate the foregoing methods of synthesis and are not to be construed as limiting the generic sense of the invention herein described.

EXAMPLE 1

Benzyl-dimethylsilylmethanamine.hydrochloride

Step A. N[(benzyl-dimethylsilyl)methyl]phthalimide (Chloromethyl)-benzyl-dimethylsilane[1] (0.420 g, 2.12 mmol) and potassium phthalimide (0.430 g, 2.32 mmol) were heated in dry dimethylformamide (DMF) (10 ml) at 70° C. for 5 hours and then the mixture was poured into water and extracted with ether. The ether solution was washed with water, dried and evaporated to give a solid mass. Recrystallization from ether/hexane afforded N-[(benzyldimethylsilyl)methyl]phthalimide as white needles (0.620 g, 94% yield, mp 91°–92° C.; 1H NMR (CDCl$_3$, TMS) δ 0.07 (s,9H), 2.20 (s,2H), 3.17 (s,2H), 6.90–7.17 (m,5H), 7.50–7.87 (m,4H).

[1] Fessenden, R. J., Coon, M. D., J. Med. Chem. Vol. 9, pg. 262–263 (1966).

Step B. A mixture of N-[(benzyl-dimethylsilyl)methyl]

phthalimide (0.620 g, 2 mmol) and hydrazine hydrate (0.120 g, 2.4 mmol) in ethanol (10 ml) was refluxed for 3 hours. 6N HCl (3 ml) was added and refluxing was continued for 30 min. Then the mixture was cooled, filtered and evaporated. Purification of the hydrochloride salt was achieved via its N-Boc derivative. Benzyl-dimethylsilylmethanamine hydrochloride was obtained as a white powder by cleavage of the N-protecting group using the method described in Step D of Example 13 (0.276 g, 64% yield); mp 138°–139° C., TLC (nBuOH-AcOH-H$_2$O, 6-2-2) 0.55; 1H NMR (CDCl$_3$, TMS) δ 0.23 (s,6H), 2.31 (s,2H), 2.36 (s,2H), 7.23–7.76 (m,5H), 8.12 (broad s, 3H).

Analysis calculated for C$_{10}$H$_{17}$NSi, HCl, C,H,N; Calc. 55.67, 8.41, 6.49; Found 55.71, 8.55, 6.

EXAMPLE 2

β-(Benzyl-dimethylsilyl)ethanamine.hydrochloride

Step A. β-(Benzyldimethylsilyl)ethanol

To a solution of benzyldimethylsilylmethyl magnesium chloride, prepared from benzylchloromethyldimethyl silane (Fessenden, R. J., Coon, M. D., J. Med. Chem. Vol. 9 pp. 262–263 (1966)) (1.5 g, 7.55 mmol) and magnesium (0.19 g, 7.9 mmol) in diethyl ether (15 ml), is added paraformaldehyde (0.228 g, 7.6 mmol). Then the mixture is refluxed for 18 hours, cooled to 0° C. and hydrolyzed with 1N HCl (25 ml). The organic layer is washed with water brine and dried over MgSO$_4$. The solution is filtered and solvent removed inuacuo. Chromatography (silica gel, hexane/diethyl ether 70/30) afforded β-(benzyldimethylsilyl)ethanol as an oil (0.84 g, 57% yield).

m.p. 132°–133° C.

Step B. N[β-(Benzyldimethylsilyl)ethyl]phthalimide

A mixture of β-(benzyldimethylsilyl)ethanol (0.84 g, 4.33 mmol), phthalimide (0.66 g, 4.5 mmol), diethylazodicarboxylate (0.783 g, 4.5 mmol) and triphenylphosphine (1.18 g, 4.5 mmol) in anhydrous tetrahydrofuran (80 ml) is stirred, under nitrogen, at room temperature for 18 hours. The solvent is removed invacuo. The residue is taken off in toluene and the insoluble material is filtered off. The filtrate is evaporated to dryness. The residue is taken off in diethyl ether and the insoluble material is filtered off. The solvent is removed in vacuo. Chromatography (silica gel, hexane/ diethyl ether—80/20) affords the title compound (0.94 g, 67% yield).

Step C. β-(Benzyldimethylsilyl )ethanamine hydrochloride

The title compound is prepared in 71% yield by a procedure similar to the one described in Example 5, Step C.

m.p. 132°–133° C.

EXAMPLE 3

β-(Dimethyl-2-phenylethylsilyl) ethanamine.hydrochloride

Step A. Chloromethyldimethyl-2-phenylethylsilane

To a solution of 2-phenylethylmagnesium bromide, prepared from 2-phenylethyl bromide (9.25 g, 50 mmol) and magnesium (1.34 g, 55 mmol) in tetrahydrofuran (50 ml), is added chlorochlormethyldimethylsilane (6.43 g, 45 mmol) in tetrahydrofuran (25 ml). The mixture is refluxed for 18 hours, cooled to 0° C. and hydrolyzed with 3N HCl (50 ml). The mixture is then poured in water (50 ml) and diethyl ether (50 ml), the organic layer is washed with water, brine, dried over MgSO$_4$ and the solvents removed invacuo. Fractional distillation affords the title compound (5.15 g, 48.5% yield).

b.p. 113°–115° C. (5 mmHg).

Step B. β-(Dimethyl-2-phenylethylsilyl)ethanol

The compound of this step is prepared in 58% yield by a procedure similar to the one described in Example 2, Step A.

Step C. β-N-[-(Dimethyl-2-phenylethylsilyl)ethyl]phthalimide

The compound of this step is prepared in 76% yield by a procedure similar to the one described in Example 2, Step B.

Step D. β-(Dimethyl-2-phenylethylsilyl)ethanamine hydrochloride

The title compound (m.p. 137°–138° C.) is prepared in 60% yield from the product of Step C by a procedure similar to the one described in Example 5, Step C.

EXAMPLE 4

Ethyl-4-fluorobenzylmethylsilylmethanamine.hydrochloride

Step A. Chlorochloromethylethylmethylsilane

A solution of ethylmagnesium bromide, prepared from ethylbromide (2.18 g, 20 mmol) and magnesium (0.49 g, 20 mmol) in diethyl ether (20 ml), is added dropwise at 0° C. to a solution of chloromethyldichloromethyl silane (3.27 g, 20 mmol) in diethyl ether (5 ml). The reaction is then refluxed for 18 hours, cooled and filtered under argon. The filtrate is concentrated by distillation at atmospheric pressure. Fractional distillation affords the title compound (2.04 g, 65.4% yield).

b.p. 125° C. (760 mmHg).

Step B. Chloromethylethyl-4-fluorobenzylmethylsilane

The compound of this step is prepared in 89% yield from the product of Step A by a procedure similar to the one described in Example 5, Step A.

Step C. N[ (4-Fluorobenzylethylmethylsilyl)methyl]phthalimide

The compound of this step is prepared in 36% yield from the product of Step B by a procedure similar to the one described in Example 5, Step B.

Step D. Ethyl-4-fluorobenzylmethylsilylmethanamine, hydrochloride

The title compound is prepared in 38% yield from the product of Step C by a procedure similar to the one described in Example 5, Step C.

m.p. 138° C.

EXAMPLE 5

Dimethyl-4-fluorobenzylsilylmethanamine.hydrochloride

Step A. Chloromethyl-dimethyl-4-fluorobenzylsilane

To the 4-fluorobenzylmagnesiumchloride, prepared from parafluorobenzylchloride (1.59 g, 11 mmol) and magnesium (0.25 g, 11 mmol) in ether (20 ml), was added dropwise, at 0° C., chloro-chloromethyl-dimethylsilane (1.43 g, 10 mmol )in ether (5 ml) Then the mixture was refluxed 6 hours, cooled to 0° C. hydrolyzed with 3N HCl (20 ml) and extracted with ether. The ether solution was washed with water, brine, dried and evaporated. Chromatography (silica gel, hexane) afforded chloromethyl-dimethyl-4-fluorobenzyl silane as an oil (2.01 g, 93% yield) 1H NMR, CDCl₃, TMS) δ: 0.20 (s,6H), 2.27 (s,2H), 2.63 (s,2H), 6.90–7.13 (m,4H).

Step B. N-[(dimethyl-4-fluorobenzylsilyl)methyl]phthalimide

Chloromethyl-dimethyl-4-fluorobenzylsilane (2.01 g, 9.33 mmol) and potassium phthalimide (1.90 g), 10.27 mmol) were heated in dry dimethylformamide (30 ml) at 70° C. for 5 hours and then the mixture was poured into water and extracted with ether. The ether solution was washed with water, brine, dried and evaporated. Chromatography (silica gel, ether/hexane—20/80) afforded N[(dimethyl-4-fluorobenzylsilyl)methyl]phthalimide as a white powder (2.90 g, 95% yield) 1H NMR (CDCl₃, TMS) δ: 0.20 (s,6H), 2.25 (s,2H), 3.27 (s,2H), 6.83–7.13 (m,4H), 7.67–7.97 (m,4H).

Step C. Dimethyl-4-fluorobenzylmethanamine.hydrochloride

A mixture of N-[(dimethyl-4-fluorobenzylsilyl)methyl] phthalimide (2.90 g, 8.88 mmol) and hydrazine hydrate (0.53 g, 10.66 mmol) in ethanol (30 ml) was refluxed for 3 hours. 6N HCl (7 ml) was added and refluxing was continued for 30 minutes. Then the mixture was cooled, filtered and evaporated. Purification of the hydrochloride salt was achieved via its N-Boc derivative. Dimethylparafluorobenzylmethanamine hydrochloride was obtained as a white powder by cleavage of the N protecting group using the method described in Step D. of Example 13. (1.25 g, 60% yield) mp 134°–135° C. 1H NMR (CDCl₃, TMS) δ: 0.20 (s,6H), 2.27 (s,2H), 2.30–2.57 (m,2H), 6.77–7.00 (m,4H), 8.07 (broad s, 3H).

EXAMPLE 6

Dimethyl-3-fluorobenzylsilylmethanamine.hydrochloride

Step A. Chloromethyldimethyl-3-fluorobenzylsilane

The compound of this step is prepared in 93% yield by a procedure similar to the one described in Example 5, Step A.

Step B. Acetoxymethyldimethyl-3-fluorobenzylsilane

Chloromethyldimethyl-3-fluorobenzylsilane (0.85 g, 3.93 mmol) and potassium acetate (0.83 g, 8.45 mmol) are refluxed in acetic acid (10 ml) for 48 hours. The mixture is then cooled, poured into water (50 ml) and extracted with diethyl ether (50 ml). The organic layer is washed with water, brine, dried over MgSO₄ and the solvent is removed invacuo. Chromatography (silica gel, hexane/ether—80/20 affords the title compound as an oil (0.38 g, 40% yield).

Step C. Dimethyl-3-fluorobenzylhydroxymethylsilane

To a mixture of lithium aluminum hydride (0.06 g, 1.58 mmol) in diethyl ether (5 ml) is added dropwise acetoxymethyldimethyl-3-fluorobenzylsilane (0.38 g, 1.58 mmol) in diethyl ether (2 ml). The mixture is then allowed to react for 0.5 hours at room temperature, treated with ethylacetate (2 ml), hydrolyzed with 1N HCl (6.5 ml), and poured into water (20 ml) and diethyl ether (10 ml). The organic layer is washed with water, brine, dried over MgSO₄ and the solvent removed in vacuo. Chromatography (silica gel, hexane/ether—60/40 affords the title compound (0.23 g, 73% yield).

Step D. N[(Dimethyl-3-fluorobenzylsilyl)methyl]phthalimide

The compound of this step is prepared in 69% yield from the product of step C by a procedure similar to the one described in Example 5, Step B.

Step E. Dimethyl-3-fluorobenzylsilylmethanamine hydrochloride

The title compound is prepared in 35% yield from the product of Step D by a procedure similar to the one described in Example 5, Step C.

m.p. 107° C.

EXAMPLE 7

α-(Benzylethylmethylsilyl)ethanamine, hydrochloride

Step A. (α-Chloroethyl)trichlorosilane

The title compound was prepared from ethyltrichlorosilane (Kipping, J. Chem Soc. 91 (1907) 214) by the method described by L. H. Sommer, F. C. Whitmore, JACS 68 (1946), 485.

Step B. (α-Chloroethyl)dichloromethylsilane

To a solution of (α-chloroethyl)trichlorosilane (1.980 g, 10 mmol) in diethyl ether (100 ml) was added a 3M solution of methylmagnesium bromide (3.3 ml). The mixture was refluxed for 12 hours, then filtered. The product was purified by distillation.

Step C. (α-Chloroethyl)chloroethylmethylsilane

To a solution of (α-chloroethyl)dichloromethylsilane (0.355 g, 2 mmol) in diethyl ether (10 ml) was added a solution of ethylmagnesium bromide (2 mmol, 1 eq). The mixture was refluxed for 12 hours, then filtered. The product was purified by distillation.

Step D. (α-Chloroethyl)benzylethylmethylsilane

To a solution of (α-chloroethyl)chloroethylmethylsilane (0.171 g, 1 mmol) in diethyl ether (5 ml) was added a solution of benzylmagnesium bromide (1 mmol, 1 eq). The mixture was refluxed for 12 hours, then filtered. The product was purified by distillation.

Step E. N[1-(Benzylethylmethylsilyl)ethyl]-phthalimide

The title compound was prepared from (α-chloroethyl)benzylethylmethylsilane and potassium phthalimide by a procedure similar to the one described in Example 1, Step A.

Step F. α-(Benzylethylmethylsilyl)ethanamine, hydrochloride

The title compound was prepared from N-[1-(benzylethylmethylsilyl)ethyl]phthalimide by a procedure similar to the one described in Example 1, Step B.

EXAMPLE 8

3,4-Difluorobenzyldimethylsilylmethanamine,. hydrochloride

Step A. Chloromethyl-3,4-difluorobenzyldimethylsilane

The compound of this step is prepared in 97% yield by a procedure similar to the one described in Example 5, Step A.

Step B. N-[(3,4-difluorobenzyldimethylsilyl)methyl]phthalimide

The compound of this step is prepared in 56% yield from the product of Step A by a procedure similar to the one described in Example 5, Step B. Step C. 3,4-Difluorobenzyldimethylsilylmethanamine, hydrochloride The title compound is prepared from the product of Step B by a procedure similar to the one described in Example 5, Step C.

m.p. 132° C.

EXAMPLE 9

2,6-Difluorobenzyldimethylsilylmethanamine, hydrochloride

Step A. Chloromethyl-2,6-difluorobenzyldimethylsilane

The title compound is prepared in 74% yield by a procedure similar to the one described in Example 5, Step A.

Step B. N[(2,6-Difluorobenzyldimethylsilyl )methyl]phthalimide

The compound of this step is prepared in 52% yield from the product of Step A by a procedure similar to the one described in Example 5, Step B.

Step C. 2,6-Difluorobenzyldimethylsilylmethanamine, hydrochloride

The title compound is prepared in 44% yield from the product of Step B by a procedure similar to the one described in Example 5, Step C. m.p. 151°–152° C.

EXAMPLE 10

2,4-Difluorobenzyl)dimethylsilylmethanamine.hydrochloride

Step A. Chloromethyl-(2,4-difluorobenzyl)dimethylsilane

The title compound is prepared in 95% yield from 2,4-difluorobenzylmagnesium chloride and chlorochloromethyldimethylsilane by the method described in Example 5, Step A.

Step B. (2,4-Difluorobenzyl)dimethylsilylmethanazide

A mixture of chloromethyl-(2,4-difluorobenzyl)dimethylsilane (11.40 g, 48.6 mmol) and sodium azide (12.64 g, 194.5 mmol) in anhydrous dimethylformamide (240 ml) is heated at 40° C. for 18 hours. Water is added to the mixture. Extraction with diethyl ether and the standard workup afforded 9.40 g of the desired compound (80% yield).

TLC: 0.59 (silica gel, ethyl acetate/cyclohexane 2:8).

Step C. N-tert-butoxycarbonyl-(2,4-difluorobenzyl)dimethylsilylmethanamine

A mixture of (2,4-difluorobenzyl)dimethylsilylmethanazide (4.65 g, 19.3 mmol) and triphenylphosphine (5.06 g, 19.3 mmol) in anhydrous tetrahydrofuran (80 ml) is stirred at room temperature, under nitrogen, for 4 hours. Water (0.52 ml) and di-t-butyldicarbonate (4.21 g, 19.3 mmol) are added and the mixture stirred at room temperature, under nitrogen for 18 hours. Water (40 ml) is added and the mixture is extracted with diethyl ether (3×80 ml). The organic layer is dried over anhydrous magnesium sulfate. Filtration and removal of the solvent in vacuo leaves an oil which is purified by chromatography (silica gel, cyclohexane). 1.89 g of the desired compound is thus obtained (30% yield).

TLC: Rf 0.43 (silica gel, ethyl acetate/cyclohexane 2:8).

Step D. (2,4-difluorobenzyl)dimethylsilylmethanamine-hydrochloride

The title compound is obtained in 90% yield from N-tert-butoxycarbonyl(2,4-difluorobenzyl)dimethylsilylmethanamine by the procedure described in Example 13, Step D. m.p.: 144° C.

EXAMPLE 11

Dimethyl-2-fluorobenzylsilylmethanamine.hydrochloride

Step A. Chloromethyldimethyl-2-fluorobenzylsilane

The compound of this step is prepared in 67% yield by a procedure similar to the one described in Example 5, Step A.

Step B. N-[Dimethyl-2-fluorobenzylsilyl)methyl]phthalimide

The compound of this step is prepared in 29% yield from the product of Step A by a procedure similar to the one described in Example 5, Step B.

Step C. Dimethyl-2-fluorobenzylsilylmethanamine, hydrochloride

The title compound is prepared in 22% yield from the product of Step B by a procedure similar to the one described in Example 5, Step m.p. 148° C.

EXAMPLE 12

Cyclohexylmethyldimethylsilylmethanamine.HCl

A mixture of benzyldimethylsilylmethanamine, HCl (5.4 g, 25.05 mmol) and amorphous platinum oxide (0,250 g) in 1M hydrochloric acid (150 ml) is stirred under hydrogen (5 psi) at room temperature for 4 days, the catalyst is then filtered and rinsed with water, and the resulting filtrate is evaporated, in vacuo. The expected amine is isolated to yield 4.20 g of product as white crystals.

m.p. 170°–172° C. TLC: Rf: 0.49 (Silica gel, AcOH/BuOH/H2O-2:6:2). Analysis calculated for $C_{10}H_{24}NSiCl$. C%: 54.14; H%: 10.90; N%: 6.31 Found C%: 54.13; H%: 11.02; N%: 6.41.

EXAMPLE 13

α-(Trimethylsilyl)benzeneethanamine.HCl

Step A. 2-Benzyl-2-trimethylsilyl-1,3-dithiane

The title compound of this step was prepared in 75% yield, by the procedure described in JACS 89, (1967), 434, by E. J. Corey, et al., using 2-benzyl-1,3-dithiane and trimethylsilyl chloride. The product was recrystallized from diethyl ether/pentane.

Step B. Benzyl-trimethylsilylketone

The title compound of this step was prepared in 73% yield by hydrolysis of 2-benzyl-2-trimethylsilyl-1,3-dithiane using mercuric chloride and mercuric oxide, following the procedure described in JACS 89, (1967), 434, by E. J. Corey, et al. The product was purified by Kugelrohr distillation.

b.p. (Kugelrohr) 170° C./16 mmHg.

Step C. N-t-butoxycarbonyl-α-(trimethylsilyl)benzeneethanamine

A mixture of benzyltrimethylsilylketone (1.40 g, 7.3 mmol) of sodium cyanoborohydride (0.321 g, 5.1 mmol) and ammonium acetate (5.93 g, 73 mmol) in anhydrous methanol (25 ml) was stirred at room temperature for 48 hours. The mixture was poured into 2N sodium hydroxide (20 ml) and extracted with diethyl ether (3×100 ml). The organic phase was dried over anhydrous magnesium sulphate. Trituration, removal of the solvent, inuacuo, and chromatography from silica gel (ethyl acetate/cyclohexane 1:1) yielded the crude α-(trimethylsilyl)benzeneethanamine which was directly converted to the product of this step using 1 equivalent of (BOC)₂O in THF. Rf: 0.74 (ethyl acetate/cyclohexane 1:1)

m.p. 67°–68° C.

Step D. A 3N solution of HCl in diethyl ether (3 ml) was added at room temperature to a mixture of N-tertbutoxycarbonyl-α-(trimethylsilyl)benzeneethanamine (0.150g, 0.51 mmol) in diethyl ether (3 ml). The mixture was stirred at room temperature for 48 hours. The resulting solid was filtered off and dried, invacuo, to yield 0.106 g of the expected α-(trimethylsilyl)-benzeneethanamine hydrochloride, m.p. 193° C.

Analysis calculated for $C_{11}H_{20}NSiCl$. C%: 57.49; H%: 8.77; N%: 6.09. Found C%: 57.40; H%: 8.56; N%: 6.01. Rf: 0.61 (AcOH/BuOH/H$_2$O,2-6-2).

Having generically described the methods of synthesis for the preparation of the compounds of Formula I and also having illustrated the generic teachings with the foregoing specific examples, it is obvious to one of ordinary skill in the art that by the appropriate modifications in the reactants, the following compounds readily will be produced:

cyclohexylmethyl diethylsilylmethanamine,
benzyldiethylsilylmethanamine,
benzylethylmethylsilylmethanamine,
4-chlorobenzyldimethylsilylmethanamine,
4-fluorobenzyldimethylsilylmethanamine,
dimethyl-4-methoxybenzylsilylmethanamine,
dimethyl-4-trifluoromethylbenzylsilylmethanamine,
dimethyl-4-hydroxybenzylsilylmethanamine,
dimethyl-4-cyanobenzylsilylmethanamine,
dimethyl-4-nitrobenzylsilylmethanamine,
3,4-difluorobenzyldimethylsilylmethanamine,
ethylmethyl-3-methyl-4-fluorobenzylsilylmethanamine,
ethylmethyl-4-fluorophenethylsilylmethanamine,
dimethyl-(3-pyridylmethyl)silylmethanamine,
dimethyl-(3-indolylmethyl)silylmethanamine,
dimethyl-(β-(5-hydroxy-3-indolyl)ethyl)silylmethanamine,
(2,4-difluorobenzyl)methylethylsilylmethanamine,
(2,4-difluorobenzyl)dimethylethylsilylmethanamine,
(2,4-difluorophenethyl)-dimethylsilylmethanamine,
(3,4-dichlorobenzyl)-dimethylsilylmethanamine,
(3,4-difluorobenzyl)-methylethylsilylmethanamine,
dimethyl-(2-furylmethyl)silylmethanamine,
dimethyl-(2-thienylmethyl)silylmethanamine,
dimethyl-(3-indazolylmethyl)silylmethanamine, as well as their corresponding silylethanamine analogs.

In its method-of-use aspect this invention relates to the use of compounds of the formula

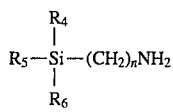

and the pharmaceutically acceptable salts thereof, wherein n is an integer 1 or 2, $R_4$ is $C_{1-10}$ alkyl, $R_5$ is $C_{1-10}$ alkyl or —$(CH_2)_m$—X,Y-substituted aryl, $R_6$ is cyclohexylmethyl or —$(CH_2)_m$—X,Y-substituted aryl, with each of X and Y being H, OH, halogeno, $C_{1-6}$ alkyl, $C_{1-6}$ alkoxy, $CF_3$, CN or $NO_2$, and m is an integer 1 to 4 as selective MAO-B inhibitors useful in the treatment of Parkinsonism and senile dementia of Alzheimer's type (DAT and SDAT).

The class of compounds known as monoamine oxidase inhibitors (MAO inhibitors) has been employed in psychiatry for over 20 years for the treatment of depression, (See Goodman and Gilman, *The Pharmacological Basis of Therapeutics,* 6th Ed., McMillan Publishing Co., Inc., N.Y., 1980, pp. 427–430). MAO inhibitors currently used in the USA for treating depression are tranylcypromine (PARNATE, SKF), phenelzine (NARDIL, Parke-Davis), and isocarboxazid (MARPLAN, Roche). In addition, another MAO inhibitor, pargyline (EUTRON, Abbott) is available for the treatment of hypertension [See *Physicians' Desk Reference,* 34th Ed., Medical Economics Co., Oradell, N.J., 1980, pp. 1327–28 (phenelzine), pp. 1466–68 (isocarboxazid) pp. 1628–1630 (tranylcypromine) and pp. 521–522 (pargyline)]. In addition to being used in treating depression, MAO inhibitors can be employed to treat other psychiatric disorders, such as phobic anxiety states.

It is believed that the MAO inhibitors act to alleviate psychiatric disorders, such as depression, by increasing the concentration of one or more biogenic monoamines in the brain or sympathetic nervous system. The monoamine oxidase enzyme (MAO) plays an important role in the metabolic regulation of the monoamines since it catalyzes the biodegradation of the monoamines through oxidative deamination. By inhibiting MAO, the degradation of the monoamines is blocked, and the result is an increase in the availability of the monoamines for their physiological functions. Among the physiologically active monoamines which are known substrates for MAO are: (a) the so-called "neurotransmitter" monoamines, such as the catecholamines (e.g., dopamine, epinephrine, and norepinephrine) and the indoleamines (e.g., tryptamine and 5-hydroxytryptamine), (b) the so-called "trace" amines (e.g., o-tyramine, phenethylamine, tele-N-methylhistamine), and (c) tyramine.

The usefulness of the MAO inhibitors in treating depression is limited because the administration of such agents can potentiate the pharmacological actions of certain food substances or drugs leading to dangerous and sometimes lethal effects. For example, persons receiving a MAO inhibitor must avoid the ingestion of foods which have a high tyramine content (such as cheese) because the MAO inhibitor will block the metabolic degradation of tyramine in the gut to produce high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy can not be given directly-acting sympathomimetic drugs (or precursors thereof) which are themselves substrates for MAO (e.g., dopamine, epinephrine, norepinephrine, or L-DOPA) and of indirectly-acting sympathomimetic drugs (e.g., amphetamines or cold, hay-fever, or weight control preparations that contain a vasoconstrictor).

The potentiation of the pressor effects of indirectly-acting sympathomimetic drugs is especially profound. This is because such drugs act peripherally primarily by releasing catecholamines in nerve endings, and the concentration of the liberated catecholamines will be dangerously elevated if the metabolic degradation of the catecholamines via MAO is blocked.

Biochemical and pharmacological studies indicate that the MAO enzyme exists in two forms known as "MAO Type A" (MAO-A) and "MAO Type B" (MAO-B). The two forms differ in their distribution in body organs, in their substrate specificity, and in their sensitivity to inhibitors. In general, MAO-A selectively oxidizes the so-called "neuro-transmitter" monoamines (epinephrine, norepinephrine, and 5-hydroxytryptamine) while MAO-B selectively oxidizes the "trace" monoamines (o-tyramine, phenethylamine, and tele-N-methylhistamine). Both MAO-A and MAO-B oxidize tyramine, tryptamine, and dopamine. However, in man, dopamine has been shown to be a preferred substrate for MAO-B. The forms also differ in their sensitivity to inhibition, and thus they can be preferentially inhibited and/or the relative concentrations of the inhibitor and the enzyme. The MAO inhibitors currently sold in the USA for the therapy of depression (tranylcypromine, phenelzine, and isocarboxazid) are not preferential in the action upon MAO. However, various chemical compounds are known in the art to be preferential inhibitors of MAO, the most important being clorgyline, pargyline, and L-deprenyl which are all reported to be clinically effective antidepressant agents. MAO-A is preferentially inhibited by clorgyline, while MAO-B is preferentially inhibited by pargyline and L-deprenyl. It should be observed that the "selectivity" of an MAO inhibitor arises because the inhibitor has a greater affinity for one form of the enzyme. Thus, the selectivity of an inhibitor for MAO-A or MAO-B in vivo will be dose-dependent, selectivity being lost as the dosage is increased. Clorgyline, pargyline, and L-deprenyl are selective inhibitors at lower dosages, but are not selective inhibitors at higher dosages. The literature concerning MAO-A and MAO-B, and the selective inhibition thereof, is extensive. [See, for example, Goodman and Gilman, ibid, pp. 204–205; Neff et al., Life Sciences, 14, 2061 (1974); Murphy, *Biochemical Pharmacology*, 27, 1889 (1978); Knoll, Chapter 10, pp. 151–171 and Sandler, Chapter 11, pp. 173–181, in *Enzyme Inhibitors as Drugs*, M. Sandler, Ed., Macmillan Press Ltd., London, 1980; Lipper et al., *Psychopharmacology*, 62, 123 (1979); Mann et al., Life Sciences, 26, 877 (1980); and various articles in *Monoamines Oxidase: Structure, Function and Altered Functions*, T. Singer et al Ed., Academic Press, N.Y., 1979].

Of the selective inhibitors of MAO, L-deprenyl is of interest since the "cheese effect" is not observed at the low dosages where preferential inhibition of MAO-B occurs. [See Knoll, TINS, pp. 111–113, May 1979]. This observation is not unexpected since the intestinal mucosa contains predominantly MAO-A which, because it is not inhibited, permits oxidation and removal of the ingested tyramine. The selectivity of L-deprenyl for MAO-B may account for its ability to potentiate L-DOPA for the treatment of Parkinson's disease without producing peripheral side effects, such as hypertension due to potentiation of pressor catecholamines [See Lees et al., Lancet, pp. 791–795, Oct. 15, 1977 and Birkmeyer, Lancet, pp. 439–443, Feb. 26, 1977].

The compounds of formulae I and 10 are pharmacologically active, being capable of inhibiting MAO as by demonstration in standard biological test procedures performed in vitro or in vivo in laboratory animals. Indeed, based upon standard laboratory procedures, the compounds of formulae I and 10 are potent and selective inhibitors of MAO-B; the inhibition being time-dependent, active site directed and irreversible. The compounds, in general, will exert their MAO inhibition within the dose range of 0.01 to 10 mg per kilogram of body weight. In particular the compounds of formula I are capable of preferentially inhibiting the B form of MAO in vitro, and in vivo, such compounds will inhibit MAO-B without substantially inhibiting MAO-A, Thus at such dosages wherein they exert a selective effect on MAO-B the compounds will not exert a marked "cheese effect". Therefore, in their end-use application of their pharmacological characteristics, the compounds of this invention (I) are useful in the treatment of Parkinson's Disease and senile dementia of Alzheimer's type (DAT and SDAT). This end-use application may be either alone or, as in the situation with L-deprenyl, in conjunction with L-DOPA. Further, the end-use application may be in conjunction with a peripheral inhibitor of L-DOPA decarboxylase (e.g., carbidopa).

Parkinson's Disease is that condition characterized by muscular rigidity, immobile facies and tremor which tends to abate on volitional movement. DAT and SDAT is an idiopathic degenerative brain disease characterized by progressive deterioration of intellectual functions and personality and in the presence of neurofibrillary tangles and amyloid plaques in the cerebral cortex and hippocampus.

For pharmacological end-use applications, the compounds of formula I are preferentially administered in the form of their pharmaceutically acceptable acid addition salts. Of course, the effective dosage of the compounds will vary according to the individual potency of each compound employed, the severity and nature of the disease being treated and the particular subject being treated. In general, effective results can be achieved by administering a compound at a dosage of about 0.05 mg to about 10 mg per kilogram of body weight per day, administered systemically. Therapy should be initiated at lower dosages. The dosage thereafter may be administered orally in solid dosage forms, e.g., capsules, tablets, or powders, in liquid forms, e.g., solutions or suspensions, or topically.

In practicing the method of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the formula 1 compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The formula 1 compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethyleneglycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl beta-aminopropionates, and 2-alkylimidazoline quarternary antmonium salts, as well as mixtures. The parenteral compositions of this invention will typically contain from about 0.5 to about 25% by weight of the formula 1 compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

As is true for most classes of compounds suitable for use as therapeutic agents, certain sub-classes and specific compounds are preferred over others. In the instant invention the preferred sub-class of compounds of formula I are those wherein $R_4$ and $R_5$ are alkyl, preferably methyl or ethyl and $R_6$ is benzyl, phenethyl, cyclohexylmethyl or pyridylmethyl or X,Y-substituted benzyl or phenethyl with X and/or Y preferably being fluoro. Specifically preferred compounds are those compounds specifically mentioned in the above specific examples 1 to 13 and β-(dimethyl-4-fluorobenzylsilyl)ethanamine, (2,4-difluorobenzyl)ethylmethylsilylmethanamine, diethyl-4-fluorobenzylsilylmethanamine, cyclohexylmethyl dimethylsilylethanamine, cyclohexylmethyl diethylsilylmethanamine, cyclohexylmethyl diethylsilylethanamine, cyclohexylmethyl ethylmethylmethanamine, and cyclohexylmethyl ethylmethylethanamine.

We claim:

1. A compound of the formula:

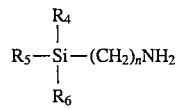

or the pharmaceutically acceptable salts thereof, wherein n is an integer 1 or 2, $R_4$ is $C_{1-6}$ alkyl, $R_5$ is $C_{1-6}$ alkyl, $R_6$ is cyclohexylmethyl or —$(CH_2)_m$—X,Y-substituted aryl, with each of X and Y being H, OH, halogeno, $C_{1-4}$ alkoxy with the proviso X and Y are not simultaneously H.

2. A compound of claim 1 wherein aryl is phenyl, furyl, thienyl, pyridyl, indolyl or indazolyl.

3. A compound of claim 1 wherein aryl is phenyl.

4. A compound of claim 3 wherein $R_6$ is benzyl or phenethyl, and one of X and Y is fluoro.

5. A compound of claim 4 wherein $R_4$ and $R_5$ are methyl or ethyl.

6. A compound of claim 1 wherein $R_6$ is cyclohexylmethyl, and $R_4$ and $R_5$ are methyl or ethyl.

7. A compound of claim 1, said compound being ethyl-4-fluorobenzylmethylsilylmethanamine.hydrochloride.

8. A compound of claim 1, said compound being dimethyl-4-fluorobenzylsilylmethanamine.hydrochloride.

9. A compound of claim 1, said compound being dimethyl-3-fluorobenzylsilylmethanamine.hydrochloride.

10. A compound of claim 1, said compound being 3,4-difluorobenzyldimethylsilylmethanamine.hydrochloride.

11. A compound of claim 1, said compound being 2,6-difluorobenzyldimethylsilylmethanamine, hydrochloride.

12. A compound of claim 1, said compound being 2,4-difluorobenzyl)dimethylsilylmethanamine.hydrochloride.

13. A compound of claim 1, said compound being dimethyl-2-fluorobenzylsilylmethanamine.hydrochloride.

14. A compound of claim 1, said compound being cyclohexylmethyldimethylsilylmethanamine.HCl.

15. A topical pharmaceutical composition in unit dosage form which comprises a compound of claim 1 and a suitable transdermal administration system.

16. A compound of claim 1 wherein m is 1, aryl is phenyl, X is H, Y is fluoro.

17. A compound of claim 1 wherein m is 1, aryl is phenyl, X is fluoro, Y is fluoro.

* * * * *

UNITED STATES PATENT AND TRADEMARK OFFICE
CERTIFICATE OF CORRECTION

PATENT NO. : 5,532,397

DATED : July 2, 1996

INVENTOR(s) : Daniel G. Schirlin, et al.

It is certified that error appears in the above-identified patent and that said Letters Patent is hereby corrected as shown below:

At column 1, line 31 and again at line 56, the patent reads "halogens" and should read --halogeno-- .
At column 4, line 37, the patent reads "paraformaidehyde" and should read --paraformaldehyde--.
At column 5, line 30, the patent reads "inuacuo" and should read --in vacuo--.
At column 5, line 40, at column 6, line 1, and at column 7, line 47, the patent reads "invacuo" and should read --in vacuo-- .
At column 10, line 12, the patent reads "Example 5, Step" and should read --Example 5, Step C--.
At column 10, line 61, the patent reads "inuacuo" and should read --in vacuo-- .
At column 11, line 6, the patent reads "invacuo" and should read --in vacuo--.
At column 15, line 41, the patent reads "antmonium" and should read --ammonium--.

Signed and Sealed this

Thirty-first Day of December, 1996

*Attest:*

BRUCE LEHMAN

*Attesting Officer*   *Commissioner of Patents and Trademarks*